United States Patent [19]

Cripps et al.

[11] Patent Number: 5,420,014
[45] Date of Patent: May 30, 1995

[54] RAPID IN VITRO TEST FOR HELICOBACTER PYLORI USING SALIVA

[75] Inventors: Allan Cripps, East Maitland; Campbell Witt, Bicton; Robert L. Clancy, New Lambton; Daniel Stiel, East Lindfield, all of Australia

[73] Assignee: Auspharm International Ltd., New South Wales, Australia

[21] Appl. No.: 876,524

[22] Filed: Apr. 30, 1992

[51] Int. Cl.$^6$ .......................................... G01N 33/569
[52] U.S. Cl. ................... 435/7.32; 435/7.9; 435/7.92; 435/7.94; 435/7.95; 436/518; 436/527; 436/530; 436/531
[58] Field of Search ............ 435/7.32, 7.9, 7.92, 435/968, 975, 7.94, 7.95; 436/518, 530, 531, 527, 528

[56] References Cited

U.S. PATENT DOCUMENTS

| | | | |
|---|---|---|---|
| 4,882,271 | 11/1989 | Evans et al. | 435/7.32 |
| 4,968,633 | 11/1990 | Marcucci | 436/513 |
| 5,200,344 | 4/1993 | Blaser et al. | 435/7.32 |

FOREIGN PATENT DOCUMENTS

329570  8/1989  European Pat. Off. ........... 435/7.32

OTHER PUBLICATIONS

B. Jones, "Fast molecule separation options", Laboratory Practice, 38(2), 64,67–68 (1989).
Evans et al. Gastroenterology, 96(4):1004—1008 (1989).
Loffeld et al. The Lancet i: 1182–1185 (May 27, 1989).
Schaber et al. Journal of Clinical Microbiology, 27(2):327–330 (Feb. 1989).
Gronblad et al. Biological Abstracts, 83(6): Abstract No. 54423 (Mar. 15, 1987).
Witt, C. S. (Aug., 1990) "The Mucosal Immune Response to *Helicobacter pylori*" in Cripps, A. W., ed. *Proceedings of a Satellite Meeting at the World Congress of Gastroenterology*, Sydney, NSW, Australia; Mucosal Immunology Abstract, pp. 149–153.
Witt, et al. (Jun. 1990) "False Positive with *Campylobacter pylori* Antibody ELISA?" in McDonald, T. T., ed., *Advances in Mucosal Immunology, Proceedings of the Fifth International Congress of Mucosal Immunology*, Abstract 250, pp. 793–794.
Czinn, et al., (May 13–19, 1989, 90th Annual Meeting of the American Gastroenterological Association), Gastroenterology, vol. 96, No. 5, Part 2 (May 1989).

*Primary Examiner*—Carol E. Bidwell
*Attorney, Agent, or Firm*—Scully, Scott, Murphy & Presser

[57] ABSTRACT

The present invention contemplates a method for detecting contempory infection by *H. pylori* in a mammal comprising contacting a mucous secretion from said mammal with an antigen component from *H. pylori* for a time and under conditions sufficient for an IgG antibody in said mucous secretion specific to said antigen component to form a complex therewith and then subjecting said complex to a detecting means. Preferably, the antigen component is immobilized onto a solid support.

17 Claims, 3 Drawing Sheets

RAPID IN VITRO TEST FOR HELICOBACTER PYLORI USING SALIVA

FIELD OF THE INVENTION

The present invention relates generally to a method which permits the rapid in vitro detection of *Helicobacter pylori* infection in mammals. More particularly, the present invention contemplates a method for the detection of IgG antibodies against *H. pylori* in mucous secretions and thereby provides a means to monitor contemporary infection by the microbe in mammals.

BACKGROUND TO THE INVENTION

Gut infections in mammals, and in particular humans, stimulate an immune response in mucous secretions, such as saliva, through activation of the common mucosal immune system. This response often initially parallels an antibody response in serum although is generally characterised by the presence of IgA antibodies. However, the immune response in secretion, including saliva, rapidly diminishes following elimination of the antigen (e.g., bacteria or virus) from the body. Accordingly, the presence of antibody in mucous secretions reflects current, i.e., contemporary, infection. In the case of a microbial infection, for example, antibodies in mucous secretions, hereinafter referred to as secretious antibodies, reflect the current status of colonisation of the microbe, such as in the gut, and thus is a useful monitor of contemporary infection. Serum antibody, on the other hand, persists for some time after the microbe is eliminated from the body. A positive serum antibody test, therefore, reflects both past and present exposure to antigen which is less helpful to the clinician. A positive secretious antibody test, on the other hand, indicates present or contemporary infection by the microbe.

The present invention arose following an investigation into *Helicobacter pylori* (also known as *Campylobacter pylori*) infection in the gut of mammals. The diagnosis of *H. pylori* infection can be made by microscopy, microbiological culture or urease detection in gastric mucosal biopsies, urea breath test or by the presence of specific antibodies in serum ELISAs. It might be predicted that *H. pylori* infection, being an infection of the gastric mucosa, would elicit an IgA antibody response in gastric secretion. However during work leading up to the present invention, it has been surprisingly discovered that the *H. pylori* specific antibody in mucous secretions is of the IgG class and not IgA as might have been expected. Little IgA antibody, if any, is detected. Accordingly, the present invention is directed to the detection of IgG in mucous secretion specific to *H. pylori* antigen and thereby provides a means of monitoring current, i.e., contempory infection by that microorganism in mammals.

A test currently available is the CLOtest (registered trademark of Delta West, Ltd., Perth, Western Australia) which detects the presence of urease in biopsy specimens. Although CLOtest is an effective monitor of *H. pylori* infection, it requires an invasive procedure, i.e., the collection of a biopsy.

In accordance with the present invention, there is provided a rapid in vitro test for contemporary *H. pylori* infection by determining the presence of specific antibodies, and in particular IgG antibodies, to the microbe in mucous secretions and thereby obviating the need for an invasive procedure.

SUMMARY OF THE INVENTION

Accordingly, in one embodiment, the present invention contemplates a method for detecting contempory infection by *H. pylori* in a mammal comprising contacting a mucous secretion from said mammal with an antigen component from *H. pylori* for a time and under conditions sufficient for an IgG antibody in said mucous secretion specific to said antigen component to form a complex therewith and then subjecting said complex to a detecting means. Preferably, the antigen component is immobilized onto a solid support.

Another embodiment of the present invention provides a test kit for detecting *H. pylori*-specific IgG antibody in mucous secretions in a mammal, said test kit comprising a solid support having an antigen component of *H. pylori* immobilized thereon, an antibody conjugated with a reporter molecule capable of producing a signal, said antibody specific against IgG antibody and optionally, when said reporter molecule is an enzyme, a substrate for said enzyme.

In a preferred embodiment, the mammal is a human. In another preferred embodiment, the antigen component comprises primarily an approximately 255–275 Kd protein and preferably a 265 Kd protein.

DETAILED DESCRIPTION OF THE INVENTION

Figure 1:
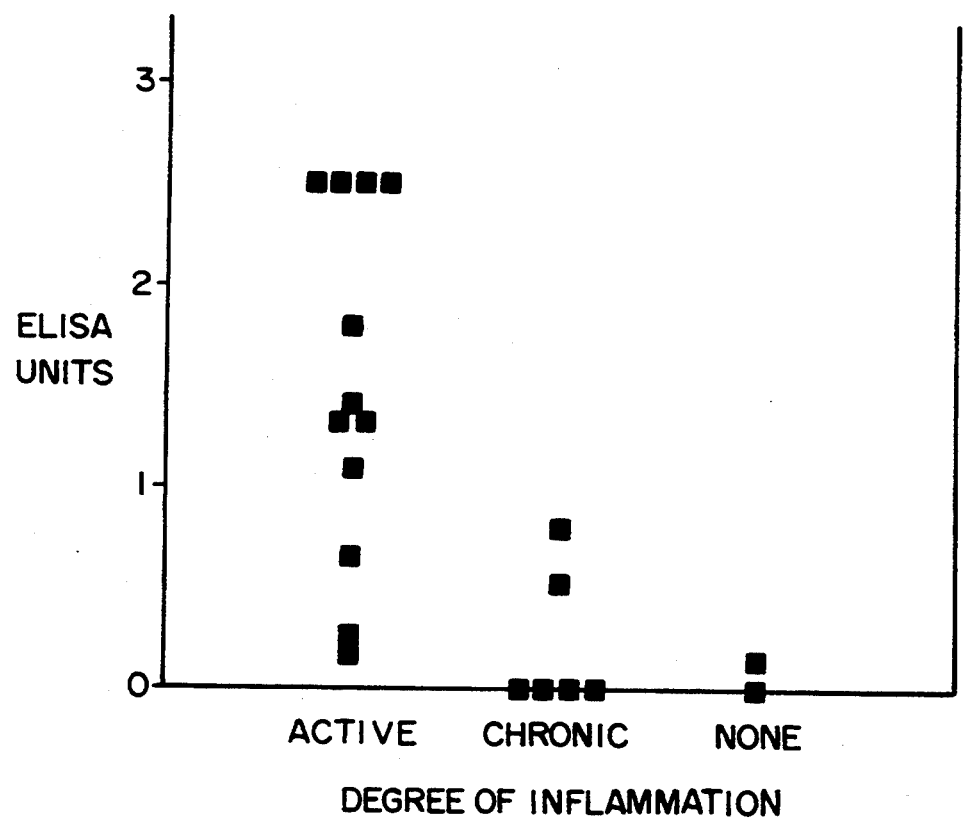
FIG. 1 is a graphical representation of the relationship between saliva ELISA scores and *H. pylori* infection. Levels of IgG antibody decrease following elimination of the bacteria from the stomach.

The present invention provides an in vitro assay for *H. pylori* infection by screening for IgG antibodies in mucous secretions. By "mucous secretion" is meant the secretion from mucous-secreting epithelial cells (i.e., mucous membrane) such as those which line the canals, cavities and tracts that communicate with the external air, and in particular the nose, throat, respiratory tract, eyes, genital and urinary passages and the digestive system. In a preferred embodiment, the mucous secretion is saliva, sputum or nasal secretion. Even more preferably, the secretion is saliva.

The solid support contemplated by the present invention includes a nitrocellulose membrane, glass or a polymer. The most commonly used polymers being cellulose, polyacrylamide, nylon, polystyrene, polyvinyl chloride or polypropylene. The solid supports may be in the form of strips, tubes, beads, discs or microplates, or any other surface suitable for conducting an immunoassay.

Antigen is used in its broadest sense and includes *H. pylori* whole cells or homogeneous, near homogeneous or heterogeneous extract from *H. pylori* and which is capable of binding to specific antibody in a mucous secretion. Antigen components contemplated by the present invention include protein, polysaccharide or lipid or any combination thereof. Preferably, the antigen is protein, lipopolysaccharide or cell extract of *H. pylori* prepared by, for example, sonication, pressure disintegration, detergent extraction or fractionation.

Preferably, the antigen component includes an approximately 255–275 Kd protein isolatable from crude *H. pylori* sonicate by FPLC. Most preferably, the molecular weight is approximately 265 Kd. The present invention extends to the naturally occurring form of this protein and to synthetic (e.g. recombinant) forms and immunologically active derivatives analogues and relatives thereof. In another preferred embodiment, an approximately 340 Kd contaminating protein is removed from the antigen preparation by, for example, freeze-drying, to which the contaminating protein is sensitive. Other techniques known to those skilled in the art may also be employed to remove the contaminating protein and/or isolate the preferred antigen component, i.e. the approximately 255–275 Kd (e.g. 265 Kd) protein. The present invention extends to synthetic (e.g. recombinant) forms or derivatives, analogues or immunological relatives of the antigen.

The antigen component of *H. pylori* contemplated by this invention is either covalently or passively bound to the solid surface. The binding processes are well-known in the art and generally consist of cross-linking, covalently binding or physically adsorbing the antigen to the solid support.

The detecting means contemplated by the present invention allows the identification of an antibody-antigen complex. This is facilitated by contacting the solid support with a second antibody, conjugated with a reporter molecule, and which is specific for at least part of the class of *H. pylori*-specific antibody found in the secretion, which, in accordance with the invention, is IgG.

By "reporter molecule" as used in the present specification is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (ie., radioisotopes). In the case of an enzyme immunoassay, an enzyme is conjugated to the second antibody, generally by means of glutaraldehyde or periodate. As will be readily recognized, however, a wide variety of different conjugation techniques exist, which are readily available to those skilled in the art. Commonly used enzymes include horseradish peroxidase, glucose oxidase, $\beta$-galactosidase and alkaline phosphatase, among others. The substrates to be used with the specific enzymes are generally chosen for the production, upon hydrolysis by the corresponding enzyme, of a detectable colour change. For example, 5-bromo-4-chloro-3-indolyl phosphate/nitroblue tetrazolium is suitable for use with alkaline phosphatase conjugates; for peroxidase conjugates, 1,2-phenylenediamine, 5-aminosalicylic acid, 3,3:5,5:tetra methyl benzidine or tolidine are commonly used. It is also possible to employ fluorogenic substrates, which yield a fluorescent product rather than the chromogenic substrates noted above. Examples of fluorogenic substrates are fluorescein and rhodamine. When activated by illumination with light of a particular wave-length, the fluorochrome-labelled antibody absorbs the light energy, inducing a state of excitability in the molecule, followed by emission of the light at a characteristic colour visually detectable with a light microscope. Immunofluorescence and EIA techniques are both well established in the art and are particularly preferred for the present method. However, other reporter molecules, such as radioisotope, chemiluminescent, and bioluminescent molecules and/or dyes and other chromogenic substances, may also be employed.

The choice of a particular reporter molecule conjugated antibody will be, for the most part, determined by the intended use and user of the test kit of the present invention. Additionally, although the test is appropriate for all mammals, it is most applicable and useful to monitoring *H. pylori* infection in humans.

Accordingly, in a preferred embodiment, the present invention provides a method for detecting contemporary infection by *H. pylori* in a human comprising contacting a mucous secretion from said human with an antigen component of *H. pylori* immobilized onto a solid support for a time and under conditions sufficient for an IgG antibody in said mucous secretion specific to said antigen component to form a complex therewith and then contacting said complex with an effective amount of a second antibody labelled with a reporter molecule and specific to the *H. pylori* specific IgG antibody and then detecting binding of said second antibody to said IgG antibody by the reporter molecule. Preferably, the mucous secretion is saliva and preferably the antigen component comprises substantially an approximately 265–275 Kd protein and preferably a 265 Kd protein from *H. pylori* or synthetic (e.g. recombinant) forms or derivatives, analogues or immunological relatives thereof.

Hence, a medical practitioner may use a nitrocellulose or other suitable solid phase support membrane strip carrying immobilized *H. pylori* antigens, such as soluble sonicate. The strip is then contacted with the mucous secretion. The strip may be placed under the tongue for a time and under conditions sufficient to allow potential *H. pylori* specific antibodies of the IgG class in saliva to bind to the immobilized antigens. Alternatively, the source of mucous secretion may be nasal secretion or sputum. The test strip, once exposed to mucous secretion, is then contacted with a second antibody conjugated with a reporter molecule for a time and under conditions sufficient for said second antibody to bind to the first antibody. Preferably, the reporter molecule is an enzyme and even more preferably alkaline phosphatase. The test strip is then washed and a substrate for the reporter molecule, or in the case where the reporter molecule is alkaline phosphatase, 5-bromo-4-chloro-3-indolyl phosphate/nitroblue tetrazolium, is contacted with the strip. The substrate reacts with the reporter molecule giving a visual signal. For example, alkaline phosphatase hydrolyses 5-bromo-4-chloro-3-indolyl phosphate to a purple product. This entire procedure can occur in the medical practitioner's office.

When a more quantitive enzyme-linked immunosorbent assay (ELISA) or immunoblot is required, such as in a clinical laboratory, a microliter tray may be used carrying immobilized *H. pylori* antigens in the wells of the tray. In this case, samples of mucous secretion, e.g., saliva, are added to the well to allow potential *H. pylori*-specific IgG antibodies to bind to the immobilized antigen. Excess secretion is washed away and a second antibody specific to IgG conjugated to a reporter molecule is added to allow an antigen-antibody-conjugated antibody complex to form. This complex is detected by adding a substrate to the reporter molecule as described above to allow, for example, a visual signal which may then be quantitated spectrophotometrically or by other means.

The present invention, especially when in the form of the nitrocellulose strip, has many advantages over the presently available assays for *H. pylori*. The use of mucous secretion, and in particular saliva, to assay for *H. pylori* antibody enables diagnosis of current or contemporary infection and thus enables the medical practitioner to:

a) Link gut symptoms with *H. pylori* which would enable decisions to be made with respect to further investigation (including invasive procedures) and/or management (e.g., use of specific anti-*H. pylori* agents). The latter may be expected to have special significance with respect to *H. pylori*-associated non ulcer dyspepsia, gastritis, duodenal ulceration, gastric ulceration and related and other conditions.

b) Have for the first time a convenient non-invasive test in the doctor's room, clinic or hospital to follow patients with proven peptic ulcer to detect early recurrence. A positive test enables early diagnosis and prevention or early treatment of recurrent peptic ulcer. A negative test has a reciprocal usefulness in analysis of the diagnostic approach to dyspepsia.

Additionally, the test contemplated by the present invention provides a simple yes/no answer, not requiring, for example, the taking of blood. It is read in minutes and developed without any special preparation of specimen by the clinician. A significant advantage of the present invention is the use of mucous secretion (e.g., saliva) to test for antibodies specific to *H. pylori*.

Hence, the present invention extends to a kit for detecting *H. pylori*-specific IgG antibody in mucous secretions in a mammal, such as a human, said test kit comprising in compartment form a first compartment adapted to contain a solid support having an antigen component of *H. pylori* immobilized thereon, a second compartment containing an antibody conjugated with a reporter molecule capable of producing a signal, said antibody specific against IgG antibody and optionally containing a third compartment, when said reporter molecule is an enzyme, containing a substrate for said enzyme. The kit may also contain additional compartments such as to receive suitable mucous material and/or for one or more diluents and/or buffers. The kit may also be packaged for sale in a suitable form. Preferably, the antigen-component is an approximately 255–275 Kd protein and most preferably a 265 Kd protein as herein described including its synthetic (e.g. recombinant) forms and/or derivatives, analogues or immunological relatives thereof.

The following examples further define the invention but should not be construed to limit the scope thereof. Comparative data are provided (Table 1) showing the efficacy of the present test relative to other procedures such as the CLOtest, histological examination, culture and an assay for antibodies in serum in patients with no evidence of *H. pylori* infection (normal gastric histology) and patients with strong evidence of *H. pylori* infection (active chronic inflammation of the gastric mucosa).

EXAMPLE 1

Enzyme-Linked Immunosorbent Assay (ELISA)

1. Preparation of *Helicobacter pylori* Antigen

Two methods of preparing *H. pylori* antigen are used: Formalinisation of whole organisms and a centrifuged sonicate.

a) Formalinisation of whole organisms
  i) *Helicobacter pylori* are harvested from chocolate agar plates into PBS.
  ii) The bacteria are washed 3 times in PBS (see 3. below) by centrifugation for 15 minutes at $2000 \times g$.
  iii) Washed bacteria are resuspended in 1% (v/v) formalin in PBS.
  iv) The suspension is incubated at ambient temperature for 30 minutes.
  v) The bacteria are washed with PBS by centrifugation.

b) Centrifuged sonicate
  i) *Helicobacter pylori* are harvested from chocolate agar plates into PBS.
  ii) The bacteria are washed 3 times in PBS by centrifugation for 15 minutes at $2000 \times g$.
  iii) Washed bacteria are resuspended in 5 ml of PBS and subject to 5 cycles of sonication (30 seconds at 6u followed by 60 seconds rest which constitutes one cycle).
  iv) Sonicated organisms are centrifuged for 15 minutes at $10,000 \times g$.
  v) The supernatant is harvested and used as the antigen preparation.

Antigen prepared by method b) is slightly superior in its ability to distinguish between saliva from infected and non-infected subjects.

2. Coating of ELISA Plates with Antigen i) Polystyrene ELISA plates are used (Polysorb, Nunc, Denmark).
  ii) Antigen is optimally diluted (highest dilution giving maximum sensitivity for antibody positive saliva without increasing reactivity of antibody negative saliva) in coating buffer (see 3. below)
  iii) An aliquot of 100 ul of diluted antigen is added to "antigen" wells of an ELISA plate and 100 ul of coating buffer (without antigen) is added to "buffer" wells.
  iv) Plates are incubated overnight at 4° C. temperature.
  v) Incubated plates are emptied, an aliquot of 100 $\mu$l of 5% w/v dried skim milk powder/coating buffer (see 3.iii below) added for 30 minutes at ambient temperature. Plates are again emptied and aliquot of 100 $\mu$l of coating buffer added and emptied immediately by flicking the contents out.

3. Buffers i) Phosphate buffered saline (PBS): 0.14M NaCl, 0.003M $Na_2HPO_4$, 0.001M $NaH_2PO_4.2H_2O$ in 1 liter of deionized water adjusted to pH 7.2.
  ii) Substrate buffer: 10.1 g citric acid, 14.2 g disodium hydrogen orthophosphate ($Na_2HPO_4$), 150 $\mu$l $H_2O_2$ (30% w/v in 1 liter of deionized water adjusted to pH 5.0.
  iii) Coating buffer: 2.42 g TRIS[tris(hydroxymethyl) amino methane], 58.44 g NaCl, in 1 liter of deionized water adjusted to pH 7.5

4. Treatment of Plates after Antigen Coating

For long term storage (6 months) of antigen coated plates, plates are dried after coating and blocking and stored at 4° C. with a dessicant. This procedure is necessary for long term preservation of the antigen coated plates.

5. ELISA Procedure a) Horse radish peroxidase method i) An aliquot of 100 ul of saliva diluted ½ in 0.05% (w/v) dried skim milk powder/PBST (PBSTM) or 100 ul of saliva diluted ½ in PBSTM is added to an antigen well and to a buffer well of the ELISA plate.

ii) Plates are incubated for up to 90 minutes at ambient temperature.

iii) Plates are washed 5 times by immersion in PBST.

iv) An aliquot of 100 ul of horse radish peroxidase anti-human IgG diluted optimally (highest dilution giving maximum sensitivity for antibody positive saliva without increasing reactivity of antibody negative saliva) in PBSTM is added to antigen and buffer wells.

v) Plates are incubated for up to 90 minutes at ambient temperature.

vi) Plates are washed 5 times by immersion in PBST.

vii) An aliquot of 100 ul of horse radish peroxidase substrate (Product T-2885, Sigma, USA) in substrate buffer is added to antigen and buffer wells.

viii) Plates are incubated for 30 minutes at ambient temperature.

ix) 100 ul of 1M $H_2SO_4$ is added to antigen and buffer wells.

x) Absorbances (A) are read using an ELISA plate reader (Titertek Multiscan MCC/340, Flow Labs, Australia).

xi) For each serum or saliva sample, the A of the buffer well is subtracted from the A of the antigen well and the resultant A is converted to ELISA units using a standard curve (constructed from doubling dilutions of a standard antibody positive serum).

xii) A survey of 100 saliva from patients who had been demonstrated by biopsy to be infected (or not infected) is used to determine the number of ELISA units corresponding to infection.

EXAMPLE 2

Immunoblotting Assay

1. Preparation of *Helicobacter pylori* Antigen

The procedure for the preparation of *H. pylori* antigen for the immunoblotting assay is identical to that for the ELISA assay (Example 1).

2. Coating of the Membrane with Antigen i) Nitrocellulose membrane is used. Nylon based membranes can also be used.

ii) The membrane is immersed in tris-buffered saline (20 mM Tris, 500 mM NaCl, pH 7.5) (TBS) for 60 seconds.

iii) After blotting dry, the membrane is soaked for 5 minutes in an optimal dilution of antigen (highest dilution of antigen giving maximum sensitivity with antibody positive samples without producing positive reactions in antibody negative samples).

iv) The membrane is then incubated for 30 minutes in 5% (w/v) skim milk powder/TBS.

v) The membrane is washed twice for 5 minutes in 0.05% (w/v) polyoxyethylene sorbitan monolaurate/TBS (TBST). For long term storage (up to 18 months) the membrane is then dried and stored at 4° C. with a desiccant.

vi) The membrane is immersed for up to 5 minutes in undiluted test saliva in a test bottle or under the tongue.

vii) The membrane is washed for 30 seconds under running tap water.

viii) The membrane is immersed in alkaline phosphatase-conjugated anti-human IgG optimally diluted (to enable distinction between antibody positive and antibody negative saliva) in PBSTM for up to 5 minutes.

ix) The membrane is washed for 30 seconds under running tap water.

x) The membrane is immersed for 5 minutes in substrate (0.3 mg nitro blue tetrazolium, 0.15 mg 5-bromo-4-chloro-3-indolyl phosphate in 1 ml 0.1M $NaHCO_3$, 1.0 mM $MgCl_2$, pH 9.8).

xi) Antibody positive samples produce a mauve colour change in the antigen region of the membrane whereas antibody negative samples do not alter the colour of the membrane in the antigen region.

EXAMPLE 3

In this experiment, the levels of IgG antibody in saliva were monitored following elimination of bacteria from the stomach.

The relationship between saliva IgG ELISA scores and *H. pylori* infection as reflected by the degree of inflammation persisting in stomach biopsies of patients with healed gastric ulcers is shown in FIG. 1.

The results clearly show that levels of IgG antibody are directly related to the level of *H. pylori* infection as indicated by the degree of gastric inflammation.

EXAMPLE 4

This example shows that the saliva ELISA is more sensitive than conventional tests for *H. pylori* infection whilst retaining the high degree of specificity of the conventional tests. The results are shown in Table 1.

TABLE 1

| TEST: DEGREE OF GASTRIC INFLAMMATION | | | |
|---|---|---|---|
| | | Normal | Active Chronic |
| CLO | − | 31 | 22 |
| (Urease test) | + | 0 | 58 |
| | % Positive | 0 | 73 |
| Culture | − | 30 | 24 |
| | + | 0 | 49 |
| | % Positive | 0 | 67 |
| Microscopy | − | 33 | 22 |
| | + | 0 | 58 |
| | % Positive | 0 | 73 |
| Serum Elisa | − | 38 | 14 |
| | + | 1 | 86 |
| | % Positive | 2.5 | 86 |
| Saliva Elisa | − | 26 | 9 |
| | + | 1 | 60 |
| | % Positive | 3.8 | 87 |

Detection of *H. pylori* by the urease test, culture, microscopy, serum ELISA and saliva ELISA in patients with no evidence of *H. pylori* infection (normal gastric histology), and patients with evidence of active *H. pylori* infection (active chronic inflammation of the gastric mucosa).

Subjects have been classified on the basis of microscopy of gastric biopsies as having active chronic inflammation, the hallmark of *H. pylori* infection, or normal gastric histology. All tests react infrequently with subjects who have normal gastric histology. However, the ELISA is more frequently positive with subjects who have active chronic inflammation than are the other tests i.e. the ELISA has a greater sensitivity.

EXAMPLE 5

In another experiment, a total of 138 patients referred to the Gastroenterology Department, Royal North Shore Hospital, NSW, for investigation of upper gastrointestinal symptoms were studied. Microbiological culture, microscopy for the detection of H. pylori urease tests, and histology of gastric biopsies and ELISAs were performed on all patients where possible. A total of 133 were tested for urease, 131 by culture, 138 by microscopy, 123 by saliva ELISA and 138 by serum ELISA.

Immunoglobulin Class of H. pylori Antibodies in Saliva

Figure 2:
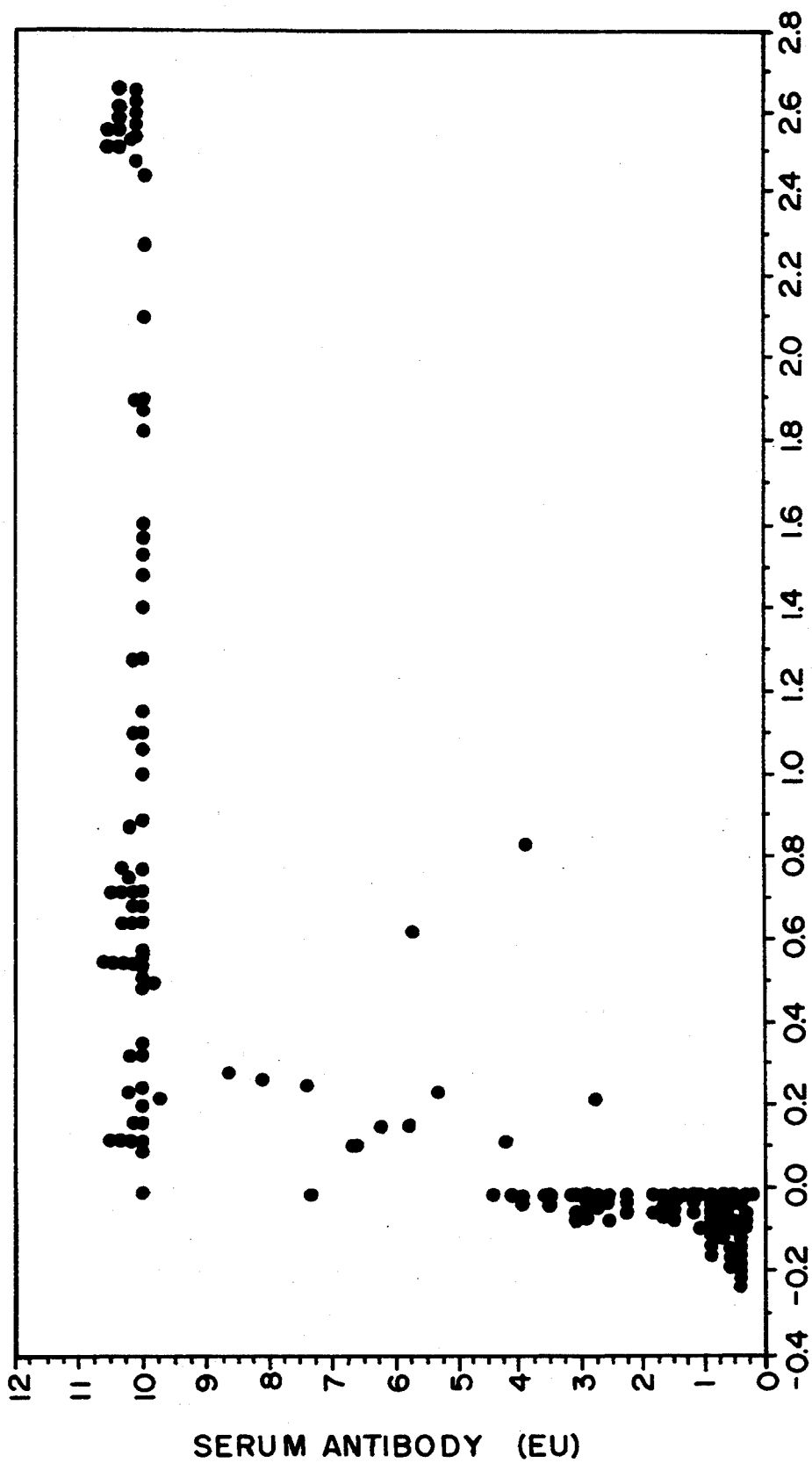
FIG. 2 is a graphical representation showing a concordance of serum and saliva antibodies.

Salivary IgA antibodies to H. pylori were found in only a minority of patients [3/18] and at very low titre. In the 3 positive salivas optical densities in wells coated with H. pylori antigen were only 0.1A units above those obtained in wells coated with coating buffet alone. Attempts to increase the sensitivity of the assay using a biotin/streptavidin system were unsuccessful. In contrast, IgG antibodies were readily detectable and their presence correlated well with the presence of IgG antibodies in serum. Using a cutoff of 0.08 units for saliva and 5 units for serum a concordance of 97% was found between 169 serum/saliva pairs (FIG. 2).

Correlation of Salivary Antibodies with Biopsy Tests for H. pylori

The relationships between gastric biopsy histology and saliva ELISA results together with other tests for H. pylori infection are shown in Table 2. The serum and saliva ELISAs were rarely positive in subjects with normal histology, positive in 30% of subjects with only chronic inflammation and over 86% of subjects with active inflammation. The other biopsy tests for H. pylori were very similar to one another; invariably negative in subjects with normal histology, positive in 4-10% of subjects with only chronic inflammation and positive in approximately 70-72% of those with active inflammation. In subjects with only chronic inflammation, the frequency of positive ELISA's increased with the severity of the chronic inflammation. Minimal/mild and moderate/severe chronic inflammation were associated with positive serum ELISAs in 2/9 and 6/8 subjects, respectively, and positive saliva ELISAs in 2/8 and 6/9 subjects, respectively.

TABLE 2

Relationship between ELISAs and biopsy tests with gastric histology

| Gastric Inflammation | Serum | | Saliva | | CLO | | Culture | | Microscopy | |
|---|---|---|---|---|---|---|---|---|---|---|
| | − | + | − | + | − | + | − | + | − | + |
| NONE | 26 | 1 | 23 | 1 | 25 | 0 | 25 | 0 | 27 | 0 |
| CHRONIC | 39 | 17 | 35 | 14 | 48 | 6 | 53 | 2 | 52 | 4 |
| ACTIVE | 7 | 48 | 7 | 43 | 15 | 39 | 15 | 36 | 16 | 39 |

EXAMPLE 6

In this experiment, a crude sonicate of H. pylori is prepared and subjected to FPLC fractionation. Western blot analysis shows that an approximately 265 Kd protein is a responsible factor in the immunological specificity of the assay of the present invention. This protein only shows reactivity in true positives unlike a contaminating 340 Kd protein. In a most preferred embodiment of the present invention, the antigen component is devoid of or substantially devoid of this 340 Kd protein. This can conveniently be achieved by freeze-drying, to which this protein appears to be sensitive.

Preparation of Helicobacter pylori Antigen

Centrifuged sonicate i) Cultures of H. pylori are harvested from chocolate agar plates in PBS. The bacteria are grown as two separate cultures, a wild strain designated "Traub" and an NCTC strain 11637.
ii) The bacteria are washed three times in PBS by centrifugation for 5 minutes at 10,000×g.
iii) Washed bacteria are resuspended in 2 ml of PBS and C.F.U.s are estimated by reading on a spectrophotometer at 405 nm.
iv) The suspension is subjected to 5 cycles of sonication (30 seconds at 6u followed by 60 seconds rest which constitutes one cycle).
v) Sonicated organisms are centrifuged for 15 minutes at 10,000×g.
vi) The supernatant is recovered and filtered through a 0.22 um filter to remove cellular debris.

FPLC Antigenic Fractions i) Sonicate is further purified by fast protein liquid chromatography on a Superose 6 size exclusion column.
ii) The column is equilibrated with PBS pH 7.2 containing 0.02% w/v sodium azide.
iii) 200 ul of sonicate are loaded onto the column and 0.5 ml fractions collected.
iv) Relevant fractions are pooled after determining the position of peak urease activity.
v) These fractions do not include the urease peak but correspond to a peak representing a group of smaller proteins with molecular weights between 440 kd and 67 kd.

Further Characterisation of Antigens i) Antigens from the above fractions are subjected to Native PAGE using linear gradient acrylamide gels and the protein profiles visualised with rapid silver staining.
ii) Relative molecular masses are estimated from standards containing thyroglobulin, ferritin, catalase, lactate dehydrogenase and albumin.
iii) Western blotting methods are employed to detect the appropriate protein bands by using sera positive to H. pylori.
iv) FPLC fractionation removes those lower molecular weight bands which are reactive with negative sera.
v) The effect of freeze drying on the antigen preparation appears to diminish the presence of a large molecular weight (about 340 Kd) unit which is reactive with false positive sera. The absence of the 340 Kd band is important in the discrimination between positive, false positive and negative sera (FIG. 3).

The effect of this purification procedure is the identification of a protein in the molecular weight range 255-275 Kd but generally about 265 Kd which is reactive to positive sera but not negative sera. See FIG. 3.

Figure 3:
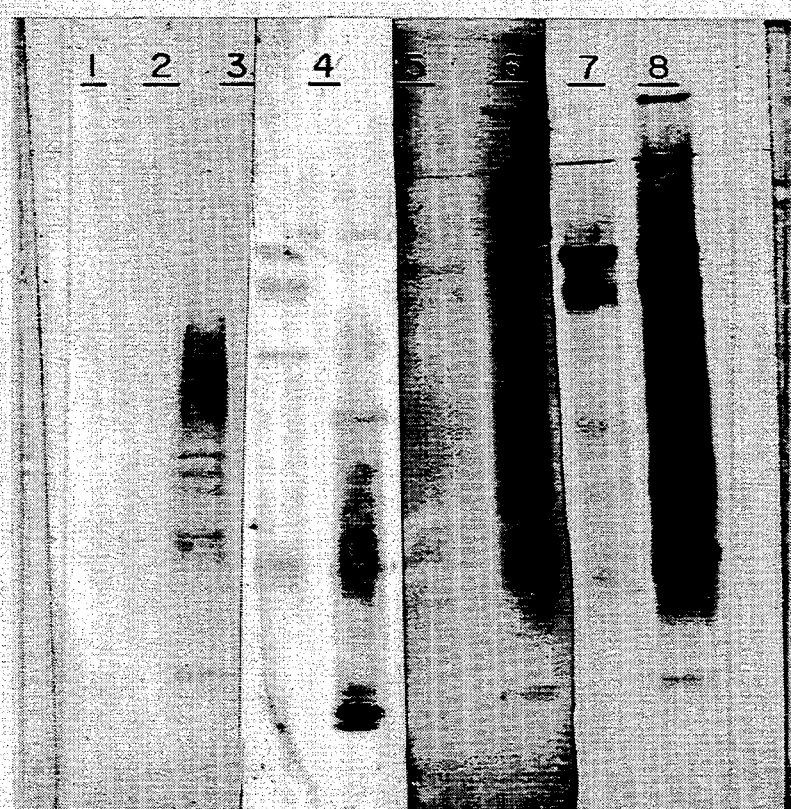
FIG. 3 is a photographic representation showing a Western blot analysis of an approximately 265 Kd antigen component from *H. pylori* purified by FPLC.

Referring to FIG. 3, channels 1, 3, 5 and 7 represent FPLC purified antigen; channels 2, 6 and 8 represent the crude sonicate of the antigen; channel 3 is purified antigen for total protein gold stain; channel 4 has high molecular weight markers for total protein gold stain; sections A, C and D have been probed with sera that is negative, false positive or positive respectively to *H. pylori* in the crude prearations there are reactive proteins which have been removed through FPLC purification, a reactive band, which has a molecular weight around 340 Kd, is still present in the purified preparation when probed with false positive sera.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

We claim:

1. A method for detecting current infection by *Helicobacter pylori* in a mammal which comprises
    contacting a sample of mucous secretion obtained from said mammal with an isolated *H. pylori*-specific antigen for a time and under conditions for formation of a complex between said antigen and anti-*H. pylori* IgG antibody present in said mucous secretion, wherein said antigen is an approximate 255 kd to an approximate 275 kd protein; and
    detecting said complex, wherein the presence of said complex indicates that said mammal is infected with *H. pylori*.

2. The method according to claim 1 wherein said antigen is an approximate 265 kd protein.

3. The method according to claim 1 wherein said antigen is immobilized onto a solid support.

4. The method according to claim 3 Wherein said solid support is a nitrocellulose membrane, glass or a polymer.

5. The method according to claim 4 wherein said polymer is cellulose, polyacrylamide, nylon, polystyrene, polyvinyl chloride or polypropylene.

6. The method according to claim 1 wherein said mucous secretion is isolated from the nose, throat, respiratory tract, eye, genital passage, urinary passage or digestive system of said mammal.

7. The method according to claim 6 wherein said mucous secretion is saliva, sputum or nasal secretion.

8. The method according to claim 7 wherein said mucous secretion is saliva.

9. The method according to claim 1 wherein said complex is detected with a second antibody which specifically binds said IgG antibody.

10. The method according to claim 9 wherein said second antibody is conjugated to an enzyme, fluorophore, radionuclide, chromophore or dye reporter molecule.

11. The method of claim 1 wherein said mammal is a human.

12. A method for detecting current infection by *Helicobacter pylori* in a human comprising:
    contacting a mucous secretion obtained from said human with an isolated *H. pylori*-specific antigen for a time and under conditions sufficient for formation of a complex between said antigen and anti-*H. pylori* IgG antibody present in said mucous secretion, wherein said antigen is an approximate 255 kd to an approximate 275 kd protein;
    contacting said complex with an effective amount of a reporter labelled second antibody which specifically binds said anti-IgG antibody; and
    detecting said second antibody bound to said IgG antibody as an indication that said mammal is infected with *H. pylori*.

13. The method according to claim 12 wherein said antigen is an approximate 265 kd protein.

14. The method according to claim 12 wherein said mucous secretion is saliva, sputum or nasal secretion.

15. The method according to claim 14 wherein said mucous secretion is saliva.

16. The method according to claim 12 wherein said reporter labelled second antibody is labelled with a reporter molecule selected from the group consisting of an enzyme, fluorophore, radionuclide, chromophore and dye.

17. The method of claim 12 wherein said antigen is immobilized onto a solid support.

* * * * *

UNITED STATES PATENT AND TRADEMARK OFFICE
CERTIFICATE OF CORRECTION

PATENT NO. : 5,420,014
DATED : May 30, 1995
INVENTOR(S) : Allan Cripps, et al.

It is certified that error appears in the above-indentified patent and that said Letters Patent is hereby corrected as shown below:

Column 4, line 56: "microliter" should read --microtitre--

Column 9, line 21: "buffet" should read --buffer--

Column 11, line 37, Claim 4: "Wherein" should read --wherein--

Signed and Sealed this

Sixteenth Day of July, 1996

*Attest:*

BRUCE LEHMAN

*Attesting Officer*     *Commissioner of Patents and Trademarks*